US012376760B2

(12) United States Patent
Umehara

(10) Patent No.: US 12,376,760 B2
(45) Date of Patent: Aug. 5, 2025

(54) MAGNETIC RESONANCE IMAGING APPARATUS, AND CONTROL METHOD FOR MAGNETIC RESONANCE IMAGING APPARATUS

(71) Applicant: CANON MEDICAL SYSTEMS CORPORATION, Tochigi (JP)

(72) Inventor: Makoto Umehara, Ota-ku (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 151 days.

(21) Appl. No.: 18/300,444

(22) Filed: Apr. 14, 2023

(65) Prior Publication Data

US 2023/0346245 A1 Nov. 2, 2023

(30) Foreign Application Priority Data

Apr. 27, 2022 (JP) .................................. 2022-073124

(51) Int. Cl.
*G01V 3/00* (2006.01)
*A61B 5/055* (2006.01)

(52) U.S. Cl.
CPC .... *A61B 5/055* (2013.01); *G06T 2207/10088* (2013.01)

(58) Field of Classification Search
CPC ...................... A61B 5/085; G06T 2207/10088
USPC ....................................................... 324/322
See application file for complete search history.

(56) References Cited

U.S. PATENT DOCUMENTS

| 8,174,264 B2 | 5/2012 | Adachi et al. |
| 2009/0322335 A1 | 12/2009 | Adachi et al. |
| 2014/0027312 A1* | 1/2014 | Macfie ............... G01N 27/3274 205/792 |

FOREIGN PATENT DOCUMENTS

| CN | 103826534 A | * | 5/2014 | ............. A61B 5/055 |
| CN | 106291418 A | * | 1/2017 | ............. G01R 33/32 |
| JP | 2010-029644 A | | 2/2010 | |
| WO | WO-2019158357 A1 | * | 8/2019 | ........... A61B 5/0013 |

* cited by examiner

*Primary Examiner* — Walter L Lindsay, Jr.
*Assistant Examiner* — Frederick Wenderoth
(74) *Attorney, Agent, or Firm* — Oblon, McClelland, Maier & Neustadt, L.L.P.

(57) ABSTRACT

A magnetic resonance imaging apparatus according to an embodiment includes a main unit and a receiver coil unit. The main unit includes processing circuitry. The processing circuitry generates a first clock signal. The processing circuitry receives a clock signal sent by the receiver coil unit in a wireless manner, and generates a second clock signal. The processing circuitry performs, in a first time period which is based on pulse sequence information, phase control of a third clock signal, based on the phase difference between the first clock signal and the second clock signal; and stops the phase control in a second time period which is based on the pulse sequence information. Then, the processing circuitry sends the third clock signal in a wireless manner to the receiver coil unit.

12 Claims, 8 Drawing Sheets

MAGNETIC RESONANCE IMAGING APPARATUS, AND CONTROL METHOD FOR MAGNETIC RESONANCE IMAGING APPARATUS

CROSS-REFERENCE TO RELATED APPLICATIONS

This application is based upon and claims the benefit of priority from Japanese Patent Application No. 2022-073124, filed on Apr. 27, 2022; the entire contents of which are incorporated herein by reference.

FIELD

Embodiments described herein relate generally to a magnetic resonance imaging apparatus and a control method for the magnetic resonance imaging method.

BACKGROUND

The magnetic resonance imaging (MRI) apparatus is an imaging apparatus configured to excite nuclear spins of a subject placed inside a static magnetic field by using radio frequency (RF) signals having the Larmor frequency, and to generate images by reconstructing the magnetic resonance (MR) signals released from the subject accompanying the excitation. In the MRI apparatus, the RF pulses are transmitted from a main unit toward the subject. Then, a receiver coil unit receives the magnetic resonance signals that are released from the subject in response to the transmission of the RF pulses. Herein, the receiver coil unit receives the magnetic resonance signals released from the subject at a position close to the subject. Depending on the imaging region of the subject, various types of receiver coil units are available, such as a receiver coil unit for the head region, a receiver coil unit for the chest region, a receiver coil unit for the spine, and receiver coil unit for the legs.

Typically, a wired-type receiver coil unit is often used that transmits the received magnetic resonance signals to the main unit in a wired manner. In contrast, a wireless-type receiver coil unit has been proposed that converts the received magnetic resonance signals, which are analog signals, into digital signals using an analog-to-digital converter, and transmits the digitized magnetic resonance signals to the main unit in a wireless manner. At the time of using a wired-type receiver coil unit, the magnetic resonance signals that are sent as analog signals from the receiver coil unit to the main unit are converted into digital signals in the main unit using a sampling clock generated from the system clock of the main unit. On the other hand, at the time of using a wireless-type receiver coil unit, the sampling clock meant for converting the magnetic resonance signals in the analog form into digital signals needs to be available in the receiver coil unit. For that, the receiver coil unit needs to have the system clock that is meant for generating a sampling clock. Besides, the system clock in the receiver coil unit and the system clock in the main unit need to be in synchronization with each other. In case phase shifting occurs between the two system clocks, there is a risk of a decline in the accuracy of the reconstructed images.

However, in the method of using a wireless-type receiver coil unit, because of the effect of phasing occurring in the wireless propagation channel, phase shifting can occur between the system clock in the receiver coil unit and the system clock in the main unit. Moreover, since a wireless-type receiver coil unit is generally battery-driven, it is desirable to achieve low power consumption.

DETAILED DESCRIPTION

An MRI apparatus according to an embodiment includes a main unit, and includes a receiver coil unit that is a separate unit from the main unit. The main unit includes a clock generating unit, a main-unit-side clock receiving unit, a clock phase control unit, a main-unit-side clock sending unit, a main-unit-side data communication unit, and an image reconstructing unit. The clock generating unit generates a first clock signal. The main-unit-side clock receiving unit receives a clock signal sent by the receiver coil unit in a wireless manner, and generates a second clock signal. The clock phase control unit performs, in a first time period which is based on pulse sequence information, phase control of a third clock signal, based on phase difference between the first clock signal and the second clock signal, and stops the phase control in a second time period which is based on the pulse sequence information. The main-unit-side clock sending unit sends the third clock signal in a wireless manner to the receiver coil unit. The main-unit-side data communication unit receives a magnetic resonance signal sent by the receiver coil unit in a wireless manner. The image reconstructing unit processes the magnetic resonance signal and reconstructs an image related to the subject.

The embodiment of the MRI apparatus and a control method for the MRI apparatus is described below in detail with reference to the accompanying drawings.

Embodiment

Figure 1:
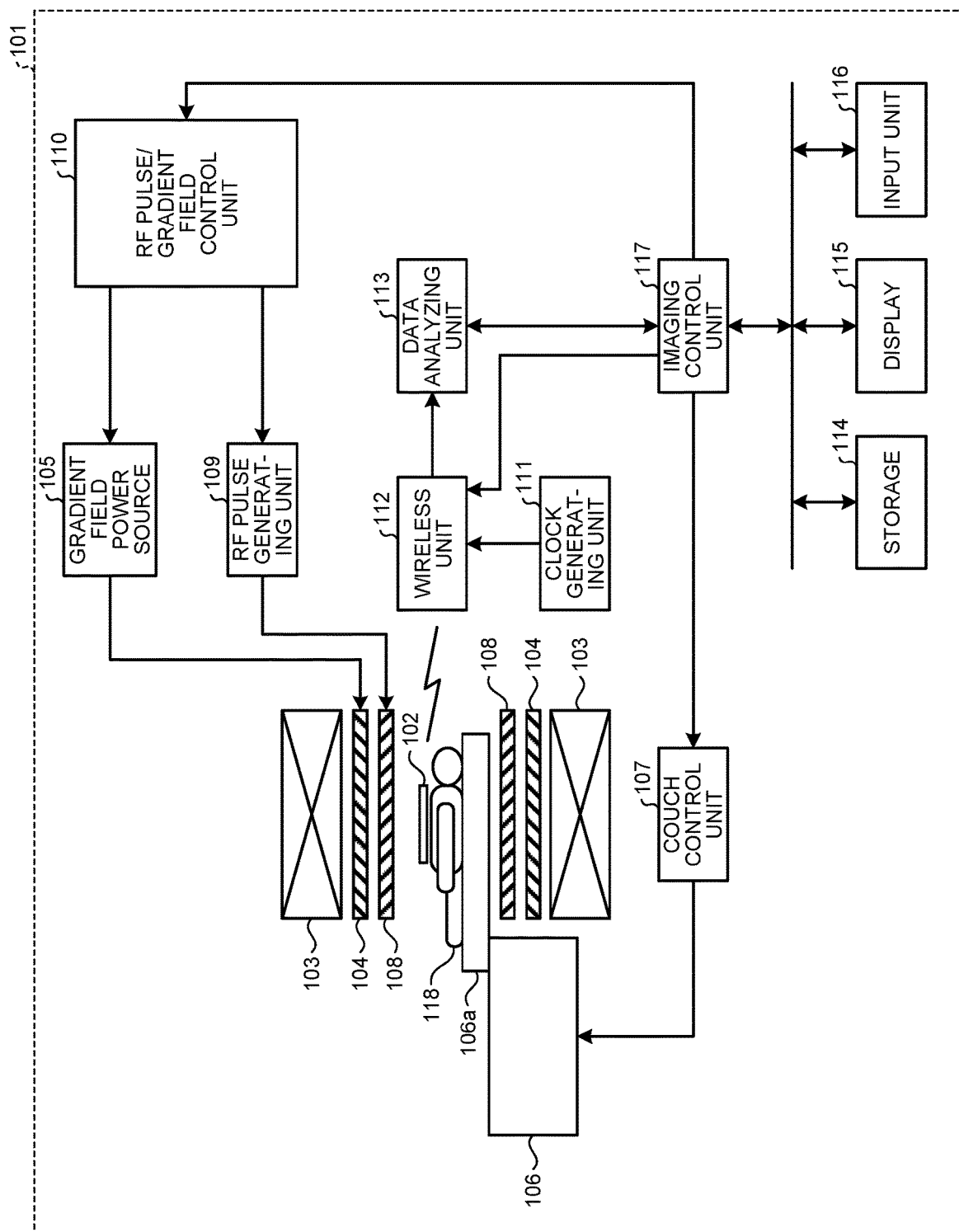
FIG. 1 is a diagram illustrating an exemplary configuration of an MRI apparatus according to an embodiment.

FIG. 1 is a diagram illustrating an exemplary configuration of the MRI apparatus according to the embodiment.

As illustrated in FIG. 1, the MRI apparatus includes a main unit 101, and includes a receiver coil unit 102 that is a separate unit from the main unit 101.

The main unit 101 includes a static magnetic field magnet 103, a gradient coil 104, a gradient field power source 105, a couch 106, a couch control unit 107, a transmitter coil 108, an RF pulse generating unit 109, an RF pulse/gradient field control unit 110, a clock generating unit 111, a wireless unit 112, a data analyzing unit 113, a storage 114, a display 115, an input unit 116, and an imaging control unit 117.

The static magnetic field magnet 103 is a hollow magnet having a cylindrical shape, and generates a uniform static magnetic field in its internal space. Examples of the static magnetic field magnet 103 include a permanent magnet and a superconducting magnet.

The gradient coil 104 is a hollow coil disposed on the inside of the static magnetic field magnet 103. The gradient coil 104 is formed by combining three types of coils corresponding to the X, Y, and Z axes that are mutually orthogonal. In the gradient coil 104, the three types of coils individually receive the supply of an electric current from the gradient field power source 105 and generate gradient fields in which the magnetic field intensity changes along the X, Y, and Z axes, respectively. Herein, the Z-axis direction is assumed to be the same direction as the gradient field direction. The gradient fields generated along the X, Y, and Z axes are, for example, a slice selection gradient field Gs, a phase encoding gradient field Ge, and a lead-out gradient field Gr, respectively. The slice selection gradient field Gs is used in arbitrarily deciding the photographing cross-section. The phase encoding gradient field Ge is used in varying the phase of a magnetic resonance signal according to the spatial position. The lead-out gradient field Gr is used in varying the frequency of a magnetic resonance signal according to the spatial position.

The couch 106 moves a couchtop 106a in the longitudinal direction (with reference to FIG. 1, the horizontal direction) and in the vertical direction under the control of the couch control unit 107. Usually, the couch 106 is installed in such a way that the longitudinal direction thereof is parallel to the central axis of the static magnetic field magnet 103. On the couchtop 106a, a subject 118 is asked to lie down. When the couchtop 106a of the couch 106 is moved, the subject 118 gets inserted in the internal space (the imaging space) of the gradient coil 104. The transmitter coil 108 is configured by housing one or more coils in a cylindrical case. The transmitter coil 108 is disposed on the inside of the gradient coil 104. The transmitter coil 108 receives the supply of RF pulse signals from the RF pulse generating unit 109, and emits RF pulses.

The RF pulse generating unit 109 generates RF pulse signals.

The RF pulse/gradient field control unit 110 controls the gradient field power source 105 and the RF pulse generating unit 109 according to pulse sequence information that is input from the imaging control unit 117. The pulse sequence information is used to define the gradient fields and the application timing of the RF pulses.

Meanwhile, herein, the explanation is given about an example in which the main unit 101 has, what is called, a tunnel-type configuration including the static magnetic field magnet 103, the gradient coil 104, and the transmitter coil 108 that have a hollow cylindrical shape. However, the embodiment is not limited by that case. Alternatively, for example, the main unit 101 can have, what is called, an open-type configuration in which a pair of static magnetic field magnets, a pair of gradient coils, and a pair of transmitter coils are placed across the imaging space in which the subject 118 is asked to lie down.

The receiver coil unit 102 is placed on the couchtop 106a, or is embedded in the couchtop 106a, or is attached to the subject 118. At the time of performing imaging, the receiver coil unit 102 gets inserted into the imaging space along with the subject 118, and receives magnetic resonance signals released from the subject 118. Thus, the receiver coil unit 102 obtains magnetic resonance signals in the electrical form. Moreover, the receiver coil unit 102 sends, in a wireless manner to the wireless unit 112, the data obtained as a result of digitizing the magnetic resonance signals. Furthermore, the receiver coil unit 102 sends wireless clock signals to and receives wireless clock signals from the wireless unit 112, and thus synchronizes the system clock with the system clock of the main unit 101.

The clock generating unit 111 generates a first clock signal having a predetermined frequency. The first clock signal is then provided to the wireless unit 112. Moreover, the first clock signal is also used as the system clock serving as the reference for the operation timings of the entire MRI apparatus.

The data analyzing unit 113 processes the obtained data and reconstructs images related to the subject 118. The data analyzing unit 113 represents an example of an image reconstructing unit.

The storage 114 is used to store a variety of data such as the image data indicating the images that have been reconstructed by the data analyzing unit 113. Examples of the storage 114 include a semiconductor memory device such as a random access memory (RAM) or a flash memory; and a memory device such as a hard disk or an optical disc.

Under the control of the imaging control unit 117, the display 115 displays the images reconstructed by the data analyzing unit 113 and displays a variety of information such as various operation screens that enable the user to operate the MRI apparatus. Examples of the display 115 include display devices such as a liquid crystal display device, a cathode-ray tube (CRT) monitor, and a touch-sensitive panel.

The input unit 116 receives various instructions and information input from the operator. Examples of the input unit 116 include the following imaging apparatuses: a pointing device such as a mouse or a trackball that enables setting the imaging conditions and the region of interest (ROI); a selection device such as a mode changing switch; a keyboard; a touchpad that enables performing an input operation by touching an operation screen; a touch-sensitive screen in which a display screen and a touchpad are integrated; a contactless input circuitry in which an optical sensor is used; and a voice input circuitry. However, in the present written description, the input unit 116 is not limited to include a physical operating component such as a mouse or a keyboard. For example, as an example of the input unit 116, it is possible to use electrical signal processing circuitry that receives electrical signals corresponding to an input operation from an external input device installed separately from the MRI apparatus, and that outputs the electrical signals to the control circuitry.

The imaging control unit 117 performs comprehensive imaging control of the MRI apparatus.

Herein, for example, in the main unit 101, each of the couch control unit 107, the RF pulse/gradient field control unit 110, the data analyzing unit 113, and the imaging control unit 117 is implemented using a processor. In that case, the processing functions of each processing unit are stored as, for example, a computer-executable program in the storage 114. Then, each processing unit reads the corresponding computer program from the storage 114 and executes it, so that the processing functions corresponding to that computer program get implemented. Meanwhile, the processing units are not limited to be implemented using singular processors. Alternatively, for example, each processing unit can be configured by combining a plurality of independent processors each of which executes a computer program and implements functions. Still alternatively, the processing functions of each processing unit can be implemented in an integrated manner in a singular processor or can be implemented in a dispersed manner among a plurality of processors. Meanwhile, herein, a single storage 114 is used to store the computer program corresponding to the processing functions. However, the embodiment is not limited by that case. Alternatively, for example, a plurality of memory units can be provided in a dispersed manner for the processing units, and each processing unit can read the corresponding computer programs from individual memory units.

Given below is the explanation of a functional configuration of the receiver coil unit 102 and a functional configuration of the wireless unit 112 included in the main unit 101.

Figure 2:
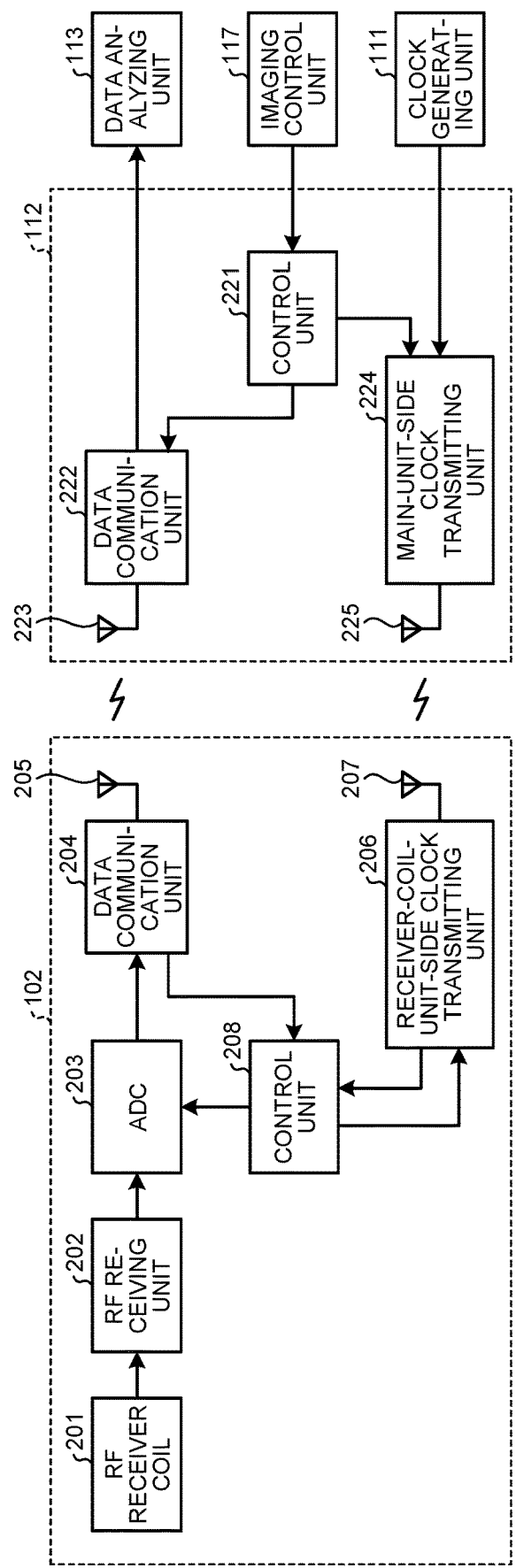
FIG. 2 is a block diagram illustrating a functional configuration of a receiver coil unit and a wireless unit according to the embodiment.

FIG. 2 is a block diagram illustrating a functional configuration of the receiver coil unit 102 and the wireless unit 112 according to the embodiment. In FIG. 2, the constituent elements identical to FIG. 1 are referred to by the same reference numerals.

As illustrated in FIG. 2, the receiver coil unit 102 includes an RF receiver coil 201, an RF receiving unit 202, an ADC 203, a data communication unit 204, a data communication antenna 205, a receiver-coil-unit-side clock transmitting unit 206, a clock transmission antenna 207, and a control unit 208. The data communication unit 204 represents an example of a receiver-coil-unit-side data communication unit.

The RF receiver coil 201 receives magnetic resonance signals that are released in the form of electromagnetic waves from the subject 118, and outputs magnetic resonance signals in the electrical form. The RF receiver coil 201 represents an example of a magnetic resonance signal detecting unit.

The RF receiving unit 202 includes a variable amplifier for amplifying the magnetic resonance signals obtained by the RF receiver coil 201, and holds down the effect of a quantization error by amplifying the magnetic resonance signals to an appropriate level in the runup to the ADC 203.

The ADC 203 performs analog-to-digital conversion of the magnetic resonance signals, which are analog signals output from the RF receiving unit 202, based on the sampling clock supplied from the control unit 208; and obtains data in the form of digital signals. The ADC 203 represents an example of an analog-to-digital conversion unit.

The data communication unit 204 is configured using a modulation-demodulation circuitry, a frequency conversion circuitry, and a power amplification circuitry. The data communication unit 204 adds a header to the data input from the ADC 203 and generates a communication frame. Then, the data communication unit 204 performs modulation and frequency conversion with respect to the communication frame so as to generate a wireless communication signal, and sends wireless communication signal to the wireless unit 112 via the data communication antenna 205. Moreover, the data communication unit 204 receives a wireless communication signal sent from the data communication unit 222 via the data communication antenna 205. Then, the data communication unit 204 performs frequency conversion and demodulation with respect to the received wireless communication signal and obtains received data. The data communication unit 204 can be configured to perform wireless communication control in conformity to the IEEE 802.11 standard. Alternatively, the data communication unit 204 can be configured to perform wireless communication control in conformity to a communication standard such as Bluetooth (registered trademark), NFC, UWB, Zigbee, or MBOA. Herein, UWB stands for Ultra Wide Band. Moreover, MBOA stands for Multi Band OFDM Alliance, in which OFDM stands for Orthogonal Frequency Division Multiplexing. Furthermore, NFC stands for Near Field Communication. The UWB involves wireless USB, wireless 1394, and Winet.

The receiver-coil-unit-side clock transmitting unit 206 sends wireless clock signals to and receives wireless clock signals from a main-unit-side clock transmitting unit 224. A wireless clock signal is a wireless signal meant for synchronizing the system clocks of the main unit 101 and the receiver coil unit 102, and is sent and received via the clock transmission antenna 207. Moreover, the receiver-coil-unit-side clock transmitting unit 206 generates a system clock from a wireless clock signal received by the clock transmission antenna 207, and outputs the system clock to the control unit 208.

The control unit 208 controls the operations of the receiver coil unit 102 based on the system clock that is output by the receiver-coil-unit-side clock transmitting unit 206. Moreover, using a PLL circuitry (PLL stands for Phase Locked Loop) (not illustrated), the control unit 208 generates a sampling clock from the system clock, and outputs the sampling clock to the ADC 203.

In the main unit 101, the wireless unit 112 includes a control unit 221, a data communication unit 222, a data communication antenna 223, the main-unit-side clock transmitting unit 224, and a clock transmission antenna 225. The data communication unit 222 represents an example of a main-unit-side data communication unit.

The control unit 221 performs wireless transmission of the pulse sequence information, which is input from the imaging control unit 117, from the data communication unit 222 to the receiver coil unit 102. Moreover, based on the pulse sequence information, the control unit 221 controls the operations of the main-unit-side clock transmitting unit 224.

The data communication unit 222 and the data communication antenna 223 have an identical configuration to the configuration of the data communication unit 204 and the data communication antenna 205, respectively. The data communication unit 222 receives wireless communication signals sent from the data communication unit 204 via the data communication antenna 223. Then, the data communication unit 222 obtains data from the received wireless communication signals, and outputs the data to the data analyzing unit 113. Moreover, the data communication unit 222 generates wireless communication signals from the pulse sequence information that is input from the control unit 221, and sends the wireless communication signals to the receiver coil unit 102 via the data communication antenna 223.

Given below is the explanation of a functional configuration of the receiver-coil-unit-side clock transmitting unit 206 and the main-unit-side clock transmitting unit 224.

Figure 3:
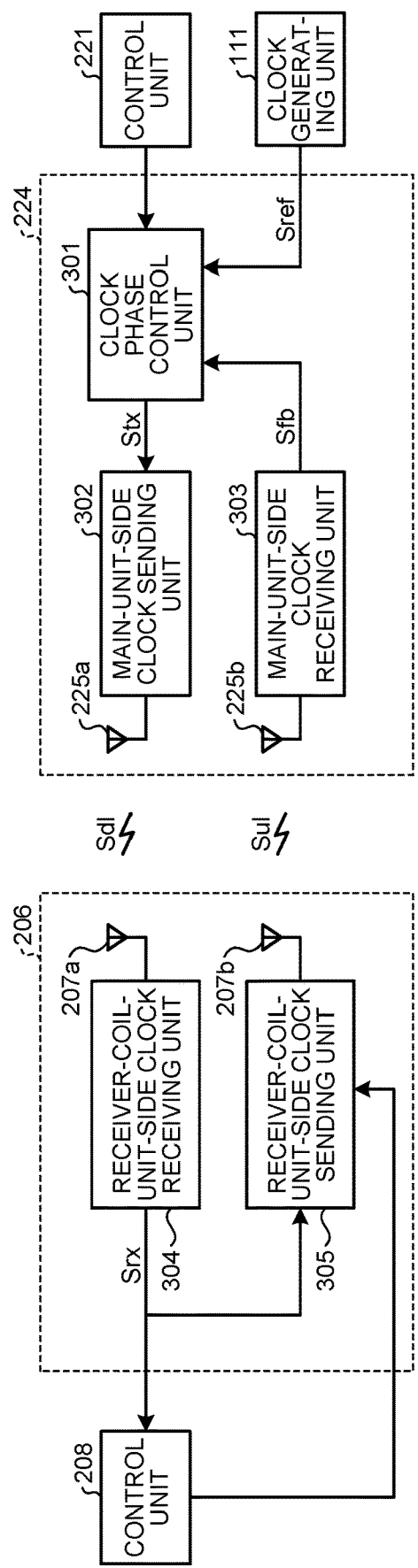
FIG. 3 is a block diagram illustrating a functional configuration of a receiver-coil-unit-side clock transmitting unit and a main-unit-side clock transmitting unit.

FIG. 3 is a block diagram illustrating a functional configuration of the receiver-coil-unit-side clock transmitting unit 206 and the main-unit-side clock transmitting unit 224.

As illustrated in FIG. 3, the main-unit-side clock transmitting unit 224 includes a clock phase control unit 301, a main-unit-side clock sending unit 302, and a main-unit-side clock receiving unit 303.

The clock phase control unit 301 generates a third clock signal Stx based on: a first clock signal Sref that is input from the clock generating unit 111; and a second clock signal Sfb that is input from the main-unit-side clock receiving unit 303. Then, the clock phase control unit 301 outputs the third clock signal Stx to the main-unit-side clock sending unit 302.

The main-unit-side clock sending unit 302 generates a wireless clock signal Sdl based on the third clock signal Stx that is input from the clock phase control unit 301; and sends the wireless clock signal Sdl to the clock transmission antenna 225a.

The main-unit-side clock receiving unit 303 uses the clock transmission antenna 225b and receives a wireless clock signal Sul that is sent by the receiver-coil-unit-side clock transmitting unit 206. Then, the main-unit-side clock receiving unit 303 generates the second clock signal Sfb from the wireless clock signal Sul, and outputs the second clock signal Sfb to the clock phase control unit 301.

The receiver-coil-unit-side clock transmitting unit 206 includes a receiver-coil-unit-side clock receiving unit 304 and a receiver-coil-unit-side clock sending unit 305.

The receiver-coil-unit-side clock receiving unit 304 uses the clock transmission antenna 207a and receives the wireless clock signal Sdl that is sent from the main-unit-side clock transmitting unit 224. Then, from the wireless clock signal Sdl, the receiver-coil-unit-side clock receiving unit 304 generates a clock signal Srx as the system clock, and outputs the clock signal Srx to the control unit 208 and the receiver-coil-unit-side clock sending unit 305.

The receiver-coil-unit-side clock sending unit 305 generates the wireless clock signal Sul based on the clock signal Srx input from the receiver-coil-unit-side clock receiving unit 304, and sends the wireless clock signal Sul using the clock transmission antenna 207b. The transmission timing of the wireless clock signal Sul is controlled by the control unit 208.

Given below is the explanation of a functional configuration of the main-unit-side clock sending unit 302 and the receiver-coil-unit-side clock sending unit 305.

Figure 4:
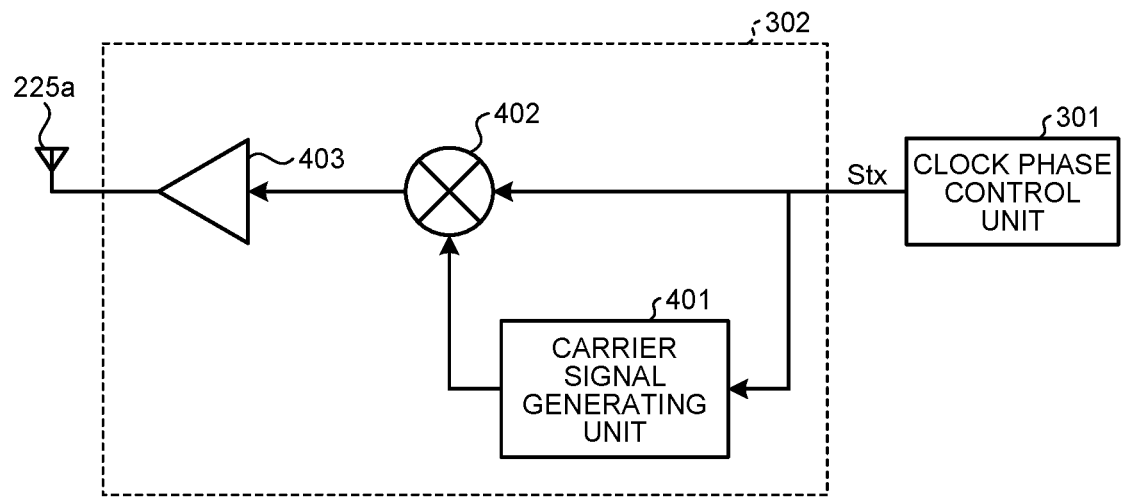
FIG. 4 is a block diagram illustrating a functional configuration of a main-unit-side clock sending unit according to the embodiment.

FIG. 4 is a block diagram illustrating a functional configuration of the main-unit-side clock sending unit 302 according to the embodiment.

As illustrated in FIG. 4, the main-unit-side clock sending unit 302 includes a carrier signal generating unit 401, a frequency mixing unit 402, and an amplifying unit 403.

The carrier signal generating unit 401 is configured using a PLL circuitry; and performs multiplication of the third clock signal Stx that is input from the clock phase control unit 301, and generates a carrier signal of the wireless frequency band.

The frequency mixing unit 402 is configured using a DBM circuitry (DBM stands for Double Balanced Mixer); and multiplies the third clock signal Stx with the carrier signal, and outputs the result to the amplifying unit 403. That is, in the embodiment, the wireless clock signal represents an amplitude-modulated signal with the third clock signal Stx functioning as the baseband signal.

The amplifying unit 403 amplifies the signal input from the frequency mixing unit 402, and sends the amplified signal as the wireless clock signal Sdl to the clock transmission antenna 225a.

Figure 5:
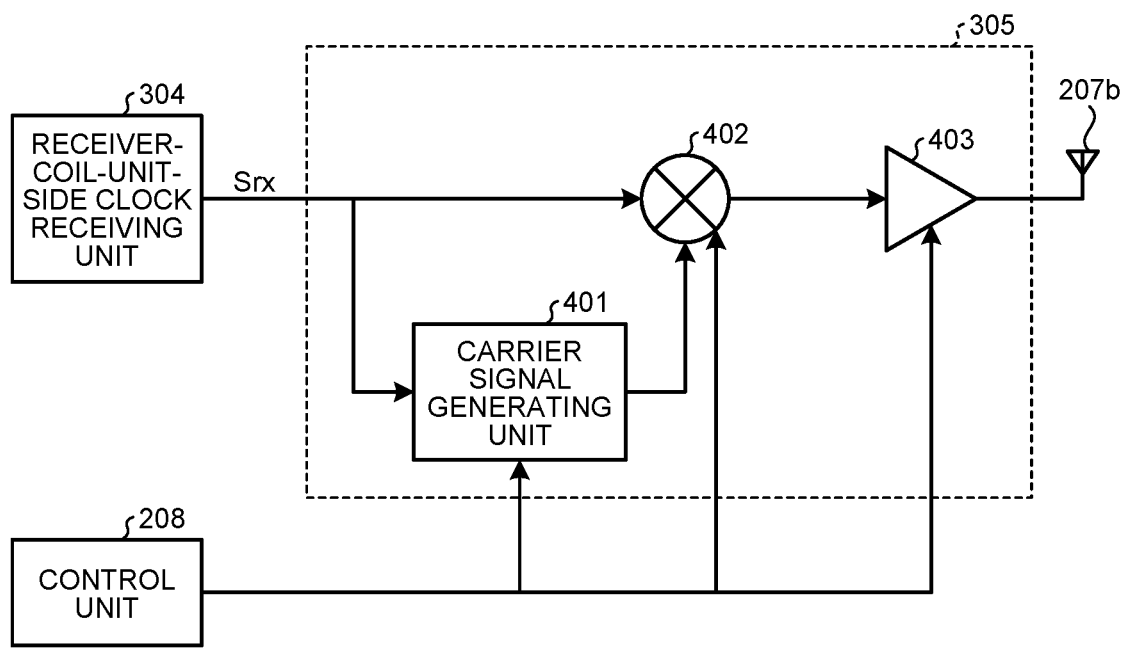
FIG. 5 is a block diagram illustrating a functional configuration of a receiver-coil-unit-side clock sending unit according to the embodiment.

FIG. 5 is a block diagram illustrating a functional configuration of the receiver-coil-unit-side clock sending unit 305 according to the embodiment. In FIG. 5, the constituent elements identical to the constituent elements of the main-unit-side clock sending unit 302 are referred to by the same reference numerals, and their explanation is not given again.

As illustrated in FIG. 5, the receiver-coil-unit-side clock sending unit 305 has an identical configuration to the configuration of the main-unit-side clock sending unit 302. However, the operations of the constituent elements of the receiver-coil-unit-side clock sending unit 305 can be temporarily stopped based on the control performed by the control unit 208, and the power consumption can be reduced as a result.

Given below is the explanation of a functional configuration of the receiver-coil-unit-side clock receiving unit 304 and the main-unit-side clock receiving unit 303.

Figure 6:
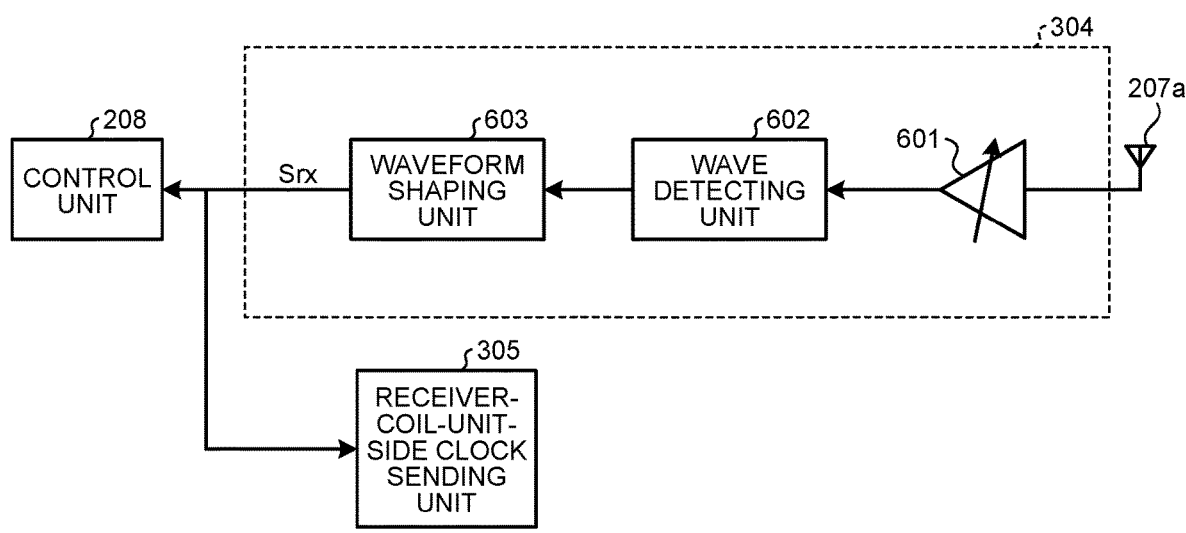
FIG. 6 is a block diagram illustrating a functional configuration of a receiver-coil-unit-side clock receiving unit according to the embodiment.

FIG. 6 is a block diagram illustrating a functional configuration of the receiver-coil-unit-side clock receiving unit 304 according to the embodiment.

As illustrated in FIG. 6, the receiver-coil-unit-side clock receiving unit 304 includes a variable gain amplifying unit 601, a wave detecting unit 602, and a waveform shaping unit 603.

The variable gain amplifying unit 601 performs level adjustment of the wireless clock signal Sdl that is received by the clock transmission antenna 207a.

The wave detecting unit 602 is configured using a diode detection circuitry or a square-law detection circuitry, and using a low pass filter (LPF). The wave detecting unit 602 performs envelope demodulation with respect to the wireless clock signal Sdl and extracts the clock signal component.

The waveform shaping unit 603 is configured using a hysteresis comparator or a PLL circuitry, and generates the clock signal Srx by performing waveform shaping of the output signal of the wave detecting unit 602. Then, the waveform shaping unit 603 outputs the clock signal Srx as the system clock to the control unit 208 and the receiver-coil-unit-side clock sending unit 305.

The main-unit-side clock receiving unit 303 has an identical configuration to the configuration of the receiver-coil-unit-side clock receiving unit 304. The main-unit-side clock receiving unit 303 generates the second clock signal Sfb from the wireless clock signal Sul, and outputs the second clock signal Sfb to the clock phase control unit 301. Given below is the explanation of the detailed operations performed by the clock phase control unit 301.

Assume that the second clock signal Sfb, the third clock signal Stx, and the clock signal Srx that is generated by the receiver-coil-unit-side clock receiving unit 304 have phases θsfb, θstx, and θsrx, respectively. In that case, the relationship among the clock signals can be expressed using Equation 1 and Equation 2 given below.

$$\theta srx = \theta stx - (\theta dtx + \theta dl + \theta drx) \qquad \text{Equation 1}$$

$$\theta sfb = \theta srx - (\theta utx + \theta ul + \theta urx) \qquad \text{Equation 2}$$

Herein, θdtx and θdrx represent the phase differences occurring due to the circuitry operation of the main-unit-side clock sending unit 302 and the receiver-coil-unit-side clock receiving unit 304, respectively. Moreover, θdl represents the phase difference caused by the wireless propagation channel. In an identical manner, θutx and θurx represent the phase differences occurring due to the circuitry operation of the receiver-coil-unit-side clock sending unit 305 and the main-unit-side clock receiving unit 303, respectively. Moreover, θul represents the phase difference caused by the wireless propagation channel.

Meanwhile, if the main-unit-side clock sending unit 302 and the receiver-coil-unit-side clock sending unit 305 have an identical configuration and if the main-unit-side clock receiving unit 303 and the receiver-coil-unit-side clock receiving unit 304 have an identical configuration, a phase difference θcircuit occurring due to those constituent elements can be expressed using Equation 3 given below. Moreover, since the wireless propagation channels are symmetrical, a phase difference θlink attributed to the symmetry can be expressed using Equation 4 given below. Moreover, the phase difference θlink occurring due to the wireless propagation channels also includes, for example, the phase fluctuation attributed to the phasing that occurs accompanying the body motion of the subject 118.

$$\theta dtx + \theta drx = \theta utx + \theta urx = \theta circuit \qquad \text{Equation 3}$$

$$\theta dl - \theta ul = \theta link \qquad \text{Equation 4}$$

Meanwhile, according to Equation 1 and Equation 2, the phase θsrx can be expressed using Equation 5 given below.

$$\theta srx = (\theta stx + \theta sfb)/2 \qquad \text{Equation 5}$$

If θsref represents the phase of the first clock signal Sref and if the phase θstx is expressed using Equation 6 given below; then the phase θsrx becomes equal to the phase θsref, and the receiver-clock-unit-side clock signal can be synchronized with the main-unit-side clock signal without getting affected by the phasing that occurs due to the wireless propagation channels.

$$\theta stx = 2 \times \theta sref - \theta sfb \qquad \text{Equation 6}$$

The clock phase control unit 301 performs operations to satisfy the condition given in Equation 6, and generates the third clock signal Stx based on the first clock signal Sref and the second clock signal Sfb.

More particularly, the clock phase control unit 301 detects a phase difference $\Delta\theta = \theta sref - \theta sfb$ between the clock signals Sref and Sfb; and generates, as Stx($\theta stx = \theta sref + \Delta\theta = 2 \times \theta sref - \theta sfb$), the clock signal obtained by advancing the phase of the clock Sref by the phase difference $\Delta\Theta$.

Meanwhile, it is assumed that the clock phase control unit 301 performs operations based on the control performed by the control unit 221; detects the phase difference $\Delta\theta$ only during a period of time in which the wireless clock signal Sul is received; and, during the remaining period of time, holds the value of the phase difference $\Delta\theta$ as detected immediately before. That is, only during the period of reception of the wireless clock signal Sul, the clock phase control unit 301 performs phase control of the clock signal Stx in such a way that the effect of the phasing is held down; and, during the remaining period of time, performs operations to stop the phase control of the clock signal Stx.

Herein, for example, the RF pulse generating unit 109, the clock generating unit 111, and the wireless unit 112 included in the main unit 101; the control unit 221, the data communication unit 222, and the main-unit-side clock transmitting unit 224 included in the wireless unit 112; the RF receiving unit 202, the ADC 203, the data communication unit 204, the receiver-coil-unit-side clock transmitting unit 206, and the control unit 208 included in the receiver coil unit 102; the clock phase control unit 301, the main-unit-side clock sending unit 302, and the main-unit-side clock receiving unit 303 included in the main-unit-side clock transmitting unit 224; the receiver-coil-unit-side clock receiving unit 304 and the receiver-coil-unit-side clock sending unit 305 included in the receiver-coil-unit-side clock transmitting unit 206; the carrier signal generating unit 401, the frequency mixing unit 402, and the amplifying unit 403 included in the main-unit-side clock sending unit 302 and the receiver-coil-unit-side clock sending unit 305; and the variable gain amplifying unit 601, the wave detecting unit 602, and the waveform shaping unit 603 included in the main-unit-side clock receiving unit 303 and the receiver-coil-unit-side clock receiving unit 304 are individually implemented using processing circuitries having the corresponding processing functions. In that case, processing circuitry implies a circuitry such as an application specific integrated circuit (ASIC) or a programmable logic device (such as a simple programmable logic device (SPLD), a complex programmable logic device (CPLD), or a field programmable gate array (FPGA)). For example, when processing circuitry is configured using an ASIC, each processing function is directly embedded as a logic circuitry in the processing circuitry. Meanwhile, processing circuitry is not limited to be configured as a single circuitry for a particular processing unit. Alternatively, single processing circuitry can be configured by combining a plurality of independent circuitries for implementing the concerned processing function. Meanwhile, a plurality of constituent elements illustrated in FIG. 4 can be integrated into single processing circuitry, and the respective processing functions can be implemented therein.

Given below is the explanation of the operations performed by the main unit 101 and the receiver coil unit 102 in the MRI apparatus according to the embodiment as configured in the manner explained above.

Figure 7:
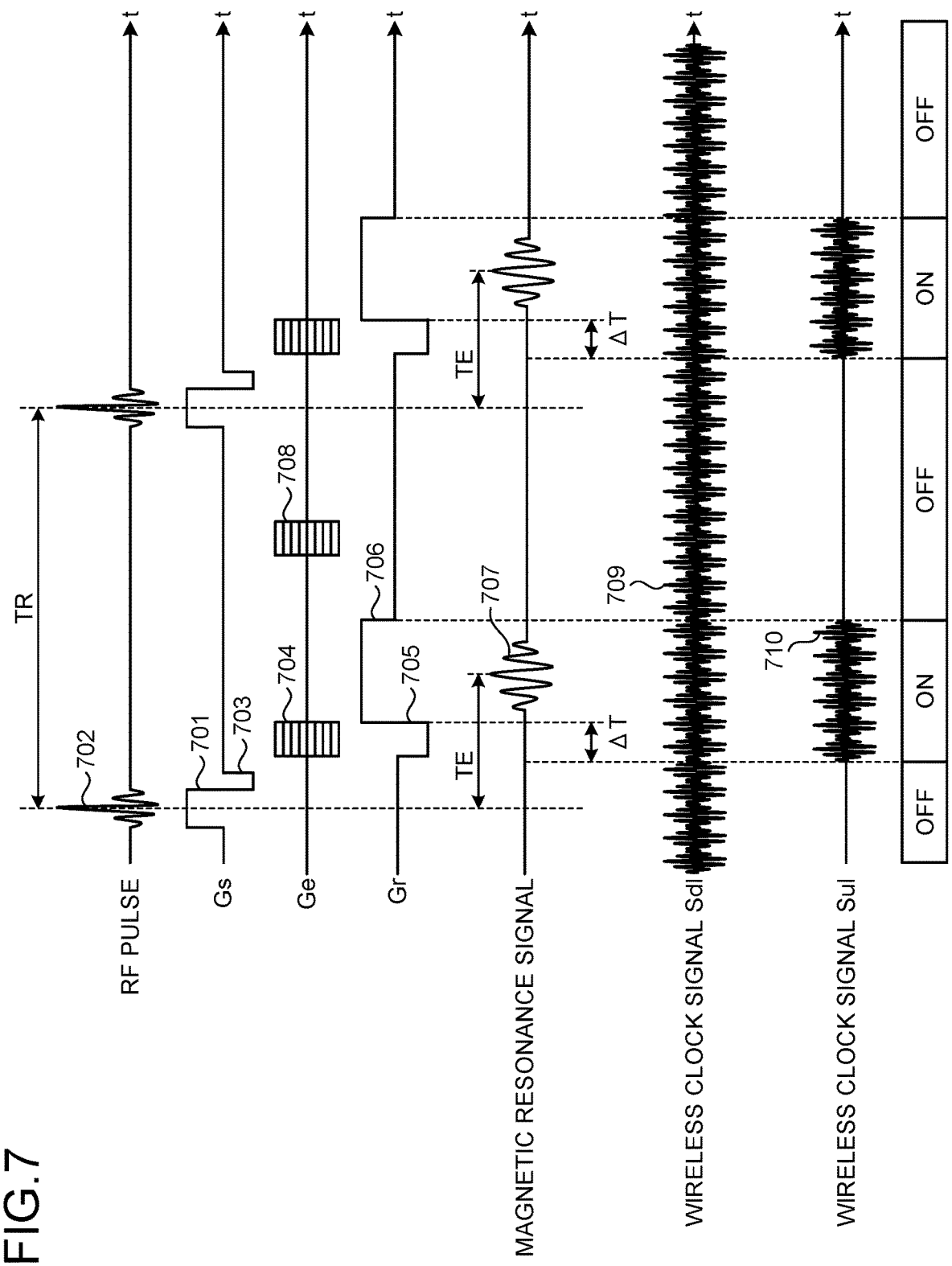
FIG. 7 is timing diagram illustrating the pulse sequence of a gradient echo method according to the embodiment.

FIG. 7 is timing diagram illustrating the pulse sequence of a gradient echo method according to the embodiment. In FIG. 7, the uppermost level represents the RF pulse; the second level from the top represents the slice selection gradient field Gs; the third level from the top represents the phase encoding gradient field Ge; the fourth level from the top represents the lead-out gradient field Gr; the fifth level from the top represents the magnetic resonance signal; the sixth level from the top represents the wireless clock signal Sdl; and the lowermost level represents the wireless clock signal Sul.

As illustrated in FIG. 7, in the pulse sequence of the gradient echo method, firstly, for example, at the same time as the application of a slice selection gradient field pulse Gs 701 having the positive polarity, an excitation RF pulse 702 having the flip angle of, for example, 90° is sent to the imaging region. Then, the transmission of the excitation RF pulse 702 is stopped and a slice selection gradient field pulse Gs 703 having the reversed polarity is applied. The slice selection gradient field pulse Gs 703 is called a rephasing lobe, and its application period is almost half of the application period of the pre-polarity-reversal slice selection gradient field pulse Gs 701. Subsequently, a phase encoding gradient field Ge 704 is applied, and a reading gradient field Gr 705 having, for example, the negative polarity is applied. Then, a reading gradient field Gr 706 having the reversed polarity is applied. Subsequently, a magnetic resonance signal 707 is released from the subject 118 around a timing during an echo period TE; and, under the application of the reading gradient field Gr 706, the magnetic resonance signal 707 is detected by the RF receiver coil 201. Subsequently, after the application of the reading gradient field Gr 706 is ended, a phase encoding gradient field Ge 708 is applied that has the opposite polarity to the phase encoding gradient field Ge 704 applied earlier. As a result, the effect of the phase encoding gradient field Ge 704, which was applied before the detection of the magnetic resonance signal 707, gets erased before the magnetic resonance signal is again collected in the next phase encoding step. This represents the collection of the magnetic resonance signal in a single phase encoding step (i.e., a single cycle), and the concerned operations are performed within a single repetition period TR illustrated in FIG. 7. This single cycle is repeated for the number of times equal to the number of phase encoding steps, so that the magnetic resonance signals corresponding to a single image are collected.

For example, in the pulse sequence explained above, the main-unit-side clock transmitting unit 224 sends a wireless clock signal Sdl 709 on a continuing basis. The receiver coil unit 102 generates a system clock from the wireless clock signals Sdl 709 and, based on the sampling clock obtained from the system clock, performs analog-to-digital conversion of the magnetic resonance signal. Herein, if there is no phasing attributed to the wireless propagation channels, in the receiver coil unit 102, it becomes possible to obtain the system clock that is synchronized with the system clock of the main unit 101.

However, in an MRI apparatus, for example, when phasing occurs due to the body motion of the subject 118, phase shifting may occur among the clocks. If such phase shifting occurs during the period of time of analog-to-digital conversion of the magnetic resonance signal 707 (i.e., during the period of application of the reading gradient field Gr 706), then it results in a decline in the accuracy of the reconstructed images.

The clock phase shifting attributed to phasing can be held down by the operations performed by the clock phase control unit 301. However, the power consumption of the receiver coil unit 102 increases due to the transmission of the wireless clock signal Sul, and any increase in the power consumption is not desirable as far as the battery-driven receiver coil unit 102 is concerned.

In that regard, in the embodiment, the receiver coil unit 102 performs operations to send the wireless clock signal Sul 710 in an intermittent manner. As a result, while holding down the power consumption of the receiver coil unit 102, the clock phase shifting is held down during the period of analog-to-digital conversion of the magnetic resonance signal 707. Meanwhile, the clock phase shifting attributed to phasing is held down after the elapse of the operation response time and the wireless signal propagation time of the main-unit-side clock sending unit 302, the main-unit-side clock receiving unit 303, the receiver-coil-unit-side clock sending unit 305, and the receiver-coil-unit-side clock receiving unit 304 since the start of the transmission of the wireless clock signal Sul. For that reason, by taking into account such factors, it is desirable to start the transmission of the wireless clock signal Sul 710 before starting analog-to-digital conversion of the magnetic resonance signal 707.

Accordingly, in FIG. 7 is illustrated an example in which the transmission of the wireless clock signal Sul 710 is started earlier, by a predetermined time period AT, than the timing of starting analog-to-digital conversion of the magnetic resonance signal 707. The predetermined time period ΔT is assumed to be set to a value equal to or greater than the total of the operation response time and the wireless signal propagation time of the constituent elements.

Meanwhile, in the embodiment, for ease of explanation, the pulse sequence of the gradient echo method is explained. However, the intermittent transmission of the wireless clock signal Sul can be implemented in an identical manner in any other type of pulse sequence such as in the spin echo method.

Figure 8:
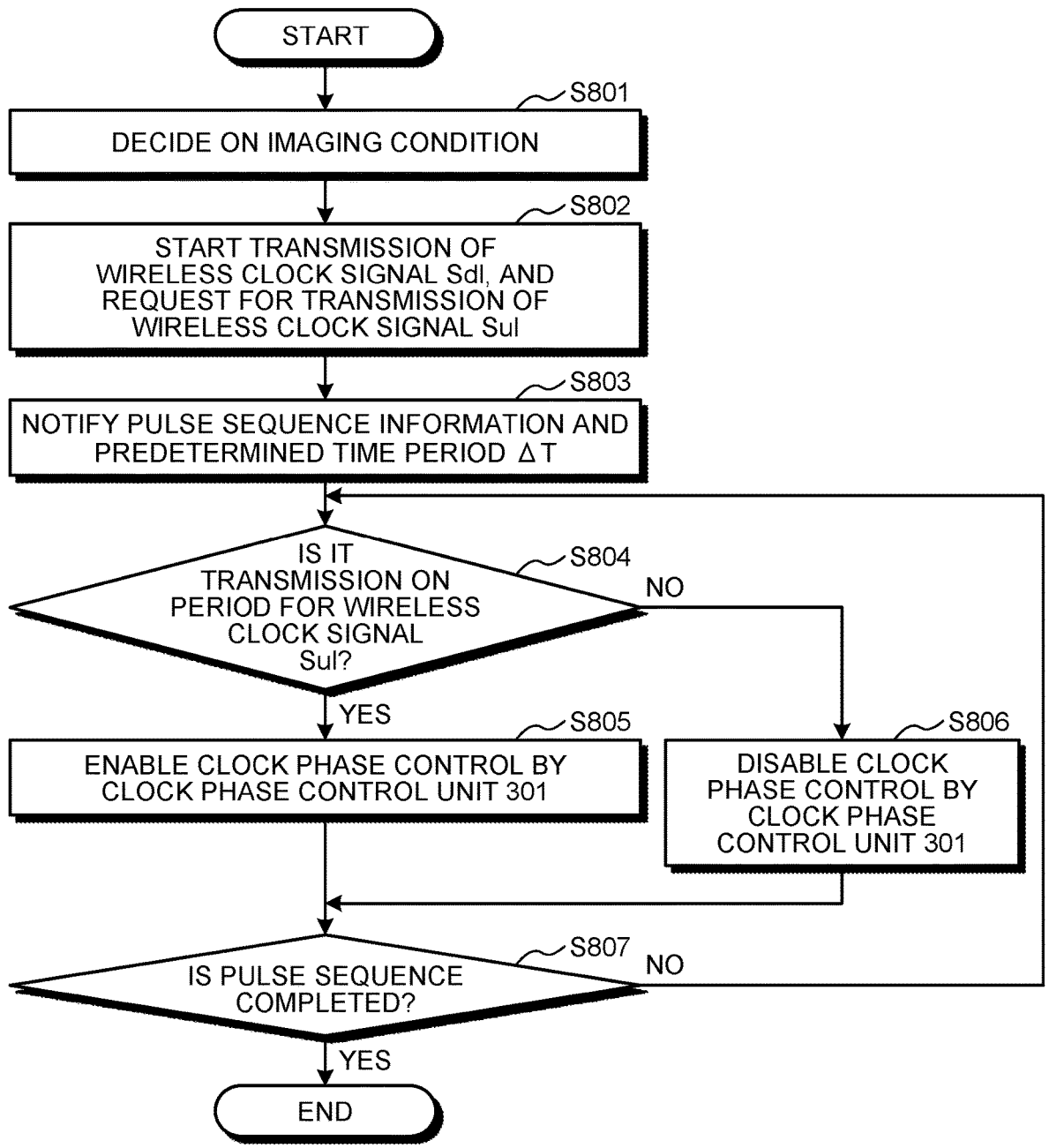
FIG. 8 is a flowchart for explaining an exemplary flow of a wireless clock signal transmission-reception operation performed by a main unit according to the embodiment.

FIG. 8 is a flowchart for explaining an exemplary flow of a wireless clock signal transmission-reception operation performed by the main unit 101 according to the embodiment. The flowchart is implemented after the subject 118 having the receiver coil unit 102 attached thereto is inserted inside the imaging region.

As illustrated in FIG. 8, at Step S801, the imaging control unit 117 decides on the pulse sequence and the predetermined time period AT, and notifies the control unit 221 about the decided pulse sequence information and the decided predetermined time period AT.

At Step S802, the control unit 221 starts the transmission of the wireless clock signal Sdl from the main-unit-side clock sending unit 302. Moreover, the control unit 221 sends, to the receiver coil unit 102, data indicating a transmission request for the wireless clock signal Sul from the data communication unit 222; and enables the clock phase control by the clock phase control unit 301.

Specifically, the clock phase control unit 301 corrects initial clock phase shifting except the effect of the phasing. Herein, initial correction amount remains held even when the clock phase control is disabled immediately.

By step S802, although the power consumption of the receiver coil unit 102 increases, by going into error processing (not illustrated) when the second clock signal Sfb is not detected, it is possible to prevent unnecessary imaging in a state where the system clock in the main unit and the system clock in the receiver coil unit are not in synchronization.

At Step S803, after the pulse sequence information and the predetermined time period AT are sent from the data communication unit 222 to the receiver coil unit 102, the control unit 221 starts a pulse sequence operation based on the pulse sequence information and the predetermined time period AT, and starts the imaging of magnetic resonance images.

At Step S804, based on the pulse sequence information and the predetermined time period AT, the control unit 221 determines whether or not it is the transmission ON period for the wireless clock signal Sul.

More particularly, based on the pulse sequence information and the predetermined time period AT, the control unit 221 sets the transmission ON period for the wireless clock signal Sul and the transmission OFF period for the wireless clock signal Sul. The control unit 221 represents an example of a main-unit-side time period setting unit. The transmission ON period for the wireless clock signal Sul represents an example of a first time period, and the transmission OFF period for the wireless clock signal Sul represents an example of a second time period.

In the embodiment, as the transmission ON period for the wireless clock signal Sul, the control unit 221 sets the period of time obtained by adding the predetermined time period AT prior to the period of time for analog-to-digital conversion of the magnetic resonance signal 707 as specified in the pulse sequence information. Moreover, the control unit 221 sets the remaining period of time as the transmission OFF period for the wireless clock signal Sul.

If it is the transmission ON period for the wireless clock signal Sul, then the system control proceeds to Step S805. On the other hand, if it is the transmission OFF period for the wireless clock signal Sul, then the system control proceeds to Step S806.

At Step S805, during the transmission ON period for the wireless clock signal Sul, the control unit 221 enables the clock phase control by the clock phase control unit 301.

At Step S806, during the transmission OFF period for the wireless clock signal Sul, the control unit 221 disables the clock phase control by the clock phase control unit 301.

At Step S807, the control unit 221 determines whether or not the collection of the magnetic resonance signal is completed in all phase encoding steps. If it is determined that the collection of the magnetic resonance signal is not completed in all phase encoding steps, then the system control returns to Step S804 and the control unit 221 continues with the pulse sequence operation. When it is determined that the collection of the magnetic resonance signal is completed in all phase encoding steps, the control unit 221 ends the pulse sequence operation.

Figure 9:
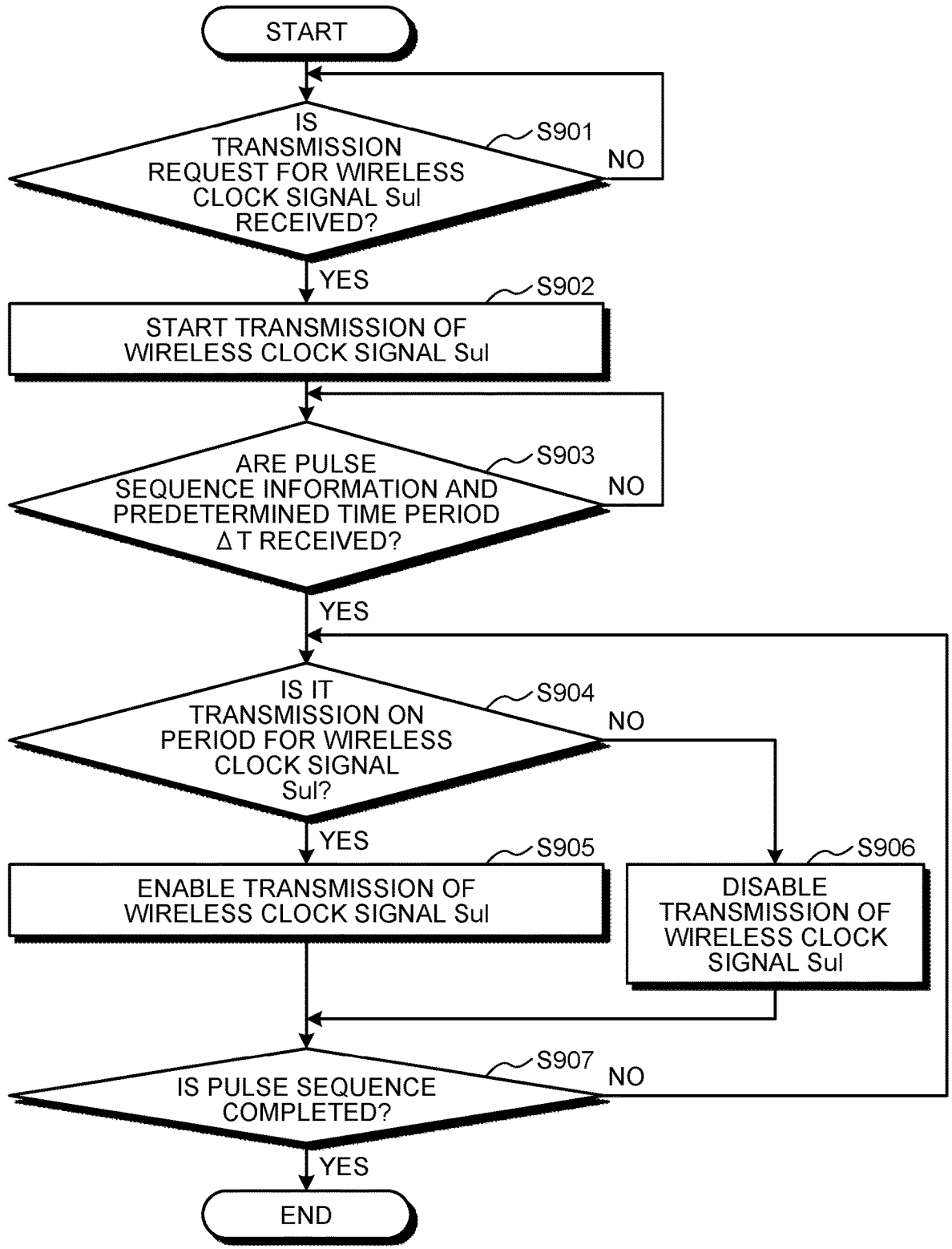
FIG. 9 is a flowchart for explaining an exemplary flow of a wireless clock signal transmission-reception operation performed by the receiver coil unit according to the embodiment.

FIG. 9 is a flowchart for explaining an exemplary flow of a wireless clock signal transmission-reception operation performed by the receiver coil unit 102 according to the embodiment.

As illustrated in FIG. 9, at Step S901, the control unit 208 waits until a transmission request for the wireless clock signal Sul is received from the main unit 101.

At Step S902, when a transmission request for the wireless clock signal Sul is received from the main unit 101, the control unit 208 starts the transmission of the wireless clock signal Sul.

At Step S903, the control unit 208 waits until the pulse sequence information and the predetermined time period ΔT are received from the main unit 101. When that information is received, the control unit 208 starts the pulse sequence operation.

At Step S904, based on the pulse sequence information and the predetermined time period ΔT, the control unit 208 determines whether or not it is the transmission ON period for the wireless clock signal Sul.

More particularly, based on the pulse sequence information and the predetermined time period ΔT, the control unit 208 sets the transmission ON period for the wireless clock signal Sul and the transmission OFF period for the wireless clock signal Sul. The control unit 208 represents an example of a receiver-coil-unit-side time period setting unit. The transmission ON period for the wireless clock signal Sul represents an example of a first time period, and the transmission OFF period for the wireless clock signal Sul represents an example of a second time period.

In the embodiment, as the transmission ON period for the wireless clock signal Sul, the control unit 208 sets the period of time obtained by adding the predetermined time period ΔT prior to the period of time for analog-to-digital conversion of the magnetic resonance signal 707 as specified in the pulse sequence information. Moreover, the control unit 208 sets the remaining period of time as the transmission OFF period for the wireless clock signal Sul.

If it is the transmission ON period for the wireless clock signal Sul, then the system control proceeds to Step S905. On the other hand, if it is the transmission OFF period for the wireless clock signal Sul, then the system control proceeds to Step S906.

At Step S905, during the transmission ON period for the wireless clock signal Sul, the control unit 208 enables the transmission of the wireless clock signal Sul by the receiver-coil-unit-side clock sending unit 305.

At Step S906, during the transmission OFF period for the wireless clock signal Sul, the control unit 208 disables the receiver-coil-unit-side clock sending unit 305 so that the transmission of the wireless clock signal Sul is stopped.

At Step S907, the control unit 208 determines whether or not the collection of the magnetic resonance signal is completed in all phase encoding steps. If it is determined that the collection of the magnetic resonance signal is not completed in all phase encoding steps, then the system control returns to Step S904 and the control unit 208 continues with the pulse sequence operation. When it is determined that the collection of the magnetic resonance signal is completed in all phase encoding steps, the control unit 208 ends the pulse sequence operation.

As a result of the operations performed by the main unit 101 and the receiver coil unit 102, the transmission of the wireless clock signals is performed at the timings illustrated in FIG. 7. With that, while holding down the power consumption of the receiver coil unit 102, it becomes possible to hold down the occurrence of clock phase shifting during the period of performing analog-to-digital conversion of the magnetic resonance signal 707.

Modification Example of Embodiment

In the embodiment, in step S802, the process may go into the error processing (not illustrated) when the second clock signal Sfb is not detected. However, step S802 can be omitted in order to reduce the power consumption of the receiver coil unit 102.

Moreover, in the embodiment, the pulse sequence information and the predetermined time period ΔT are notified from the main unit 101 to the receiver coil unit 102. However, the embodiment is not limited by that configuration. For example, a user interface (UI) can be provided in the receiver coil unit 102, so that the operator can use the user interface for setting the pulse sequence information and the predetermined time period ΔT.

Moreover, in the embodiment, transmission and reception of wireless signals is performed in the following three links: the link between the data communication unit 204 and the data communication unit 222; the link between the main-unit-side clock sending unit 302 and the receiver-coil-unit-side clock receiving unit 304; and the link between the receiver-coil-unit-side clock sending unit 305 and the main-unit-side clock receiving unit 303. In that regard, it is desirable that the wireless signals among the links are mutually isolated so as to ensure that they do not affect each other. For example, it is possible to implement the frequency division multiplexing (FDM) method in which isolation is guaranteed by using a different carrier frequency in each link. Alternatively, it is possible to implement the space division multiplexing (SDM) method in which isolation is guaranteed based on the antenna directionality of each link. In the case of isolating the links according to the FDM method, a filter device such as a diplexer or a triplexer can be used so as to enable sharing of the antennas of the links.

Furthermore, in the embodiment, it is assumed that the wireless clock signals represent amplitude-modulated signals. However, the embodiment is not limited by that case. Alternatively, it is possible to use frequency-modulated signals. In that case, for example, a clock sending unit is configured to generate a frequency-modulated baseband signal with the third clock signal Stx functioning as the signal wave, and to input the frequency-modulated baseband signal to the frequency mixing unit 402. Moreover, the wave detecting unit 602 is configured using a PLL circuit, and extracts the clock signal component based on PLL wave detection.

Moreover, in the embodiment, the wave detecting unit 602 generates a clock signal by performing a wave detection operation. However, the embodiment is not limited by that case. Alternatively, a clock signal can be generated from a carrier signal. In that case, the wave detecting unit 602 is changed to, for example, a clock regenerating unit including a Costas loop circuit and a divider circuit. As a result, a carrier signal can be regenerated from a wireless clock signal, and the regenerated carrier signal can be divided so as to generate a clock signal having the same frequency as the system clock.

Furthermore, in the embodiment, the predetermined time period ΔT is set to a value equal to or greater than the total of the operation response time and the wireless signal propagation time of the main-unit-side clock sending unit 302, the main-unit-side clock receiving unit 303, the receiver-coil-unit-side clock sending unit 305, and the receiver-coil-unit-side clock receiving unit 304. However, the embodiment is not limited by that case. Alternatively, for example, after Step S802 illustrated in FIG. 8, a ΔT setting step for can be additionally performed to measure the period of time that should be set as the predetermined time period ΔT. In that case, for example, in the ΔT setting step, the control unit 221 instructs the clock phase control unit 301 to vary the phase of the third clock signal Stx. This phase variation appears in the second clock signal Sfb after the elapse of the operation response time and the wireless signal propagation time of the constituent elements. Thus, after the clock phase control unit 301 has started the phase control of the third clock signal Stx, the control unit 221 measures the operation response time and the wireless signal propagation time until the phase control appears as the phase variation of the second clock signal Sfb, and then decides on the predetermined time period ΔT based on the measurement result of the operation response time and the wireless signal propagation time. Thus, the control unit 221 represents an example of a time measuring unit.

Moreover, in the embodiment, the predetermined time period ΔT is set to a value equal to or greater than the total of the operation response time and the wireless signal propagation time of the main-unit-side clock sending unit 302, the main-unit-side clock receiving unit 303, the receiver-coil-unit-side clock sending unit 305, and the receiver-coil-unit-side clock receiving unit 304; and the control unit 221 of the main unit 101 as well as the control unit 208 of the receiver coil unit 102 sets, as the transmission ON period for the wireless clock signal Sul, the period of time obtained by adding the predetermined time period ΔT prior to the period of time for analog-to-digital conversion of the magnetic resonance signal 707 as specified in the pulse sequence information. However, the embodiment is not limited by that case. Alternatively, for example, a period of time equal to or greater than the operation response time of the constituent elements can be set as the predetermined time period ΔT, or a period of time equal to or greater than the wireless signal propagation time of the constituent elements can be set as the predetermined time period ΔT. Still alternatively, for example, as the transmission ON period for the wireless clock signal Sul, the control unit 221 as well as the control unit 208 either can set the period of time for analog-to-digital conversion of the magnetic resonance signal 707 as specified in the pulse sequence information or can set the period of time obtained by adding a predetermined preparatory period of time to the period of time for analog-to-digital conversion. That is, the control unit 221 and the control unit 208 can set the first time period based on at least one of the following: the period of time for analog-to-digital conversion of a magnetic resonance signal as specified in the pulse sequence information; the operation response time of the main-unit-side clock sending unit 302, the main-unit-side clock receiving unit 303, the receiver-coil-unit-side clock sending unit 305, and the receiver-coil-unit-side clock receiving unit 304; and the wireless signal propagation time of the main-unit-side clock sending unit 302, the main-unit-side clock receiving unit 303, the receiver-coil-unit-side clock sending unit 305, and the receiver-coil-unit-side clock receiving unit 304.

Furthermore, in the embodiment, based on the pulse sequence information and the predetermined time period ΔT as sent from the control unit 221 of the main unit 101, the control unit 208 of the receiver coil unit 102 sets the transmission ON period and the transmission OFF period for the wireless clock signal Sul. However, the embodiment is not limited by that case. Alternatively, the control unit 221 of the main unit 101 can send, to the receiver coil unit 102, the transmission ON period and the transmission OFF period for the wireless clock signal Sul as set in the main unit 101. In that case, using the transmission ON period and the transmission OFF period sent from the control unit 221 of the main unit 101, the control unit 208 of the receiver coil unit 102 controls the transmission of the wireless clock signal Sul as performed by the receiver-coil-unit-side clock sending unit 305.

Moreover, in the embodiment, a period of time including the period of time for analog-to-digital conversion of the magnetic resonance signal 707 is set as the transmission ON period for the wireless clock signal Sul. However, the embodiment is not limited by that case. Alternatively, for example, during a particular period of time, as long as the accuracy of the reconstructed images can be enhanced as a result of reducing the clock phase shifting, a period of time not including the period of time for analog-to-digital conversion of the magnetic resonance signal 707 can also be set as the transmission ON period for the wireless clock signal Sul.

Furthermore, in the embodiment, the explanation is given about the example in which the receiver coil unit communicates data and the clocks in a wireless manner. However, it is also possible to have a wireless-type receiver coil unit as well as a wired-type receiver coil unit. Regarding the wired-type receiver coil unit, a magnetic resonance signal is sent as an analog signal from the receiver coil unit to the main unit, and is subjected to analog-to-digital conversion in the main unit using the sampling clock generated from the system clock in the main unit. For example, in the case of performing imaging of a body area, there are times when a wired-type receiver coil unit is used as the coil unit for the backside, and a wireless-type receiver coil unit is used as the coil unit for the frontside. That is because using a wireless-type receiver coil unit on the frontside is more effective in regard to the clinical usability. Such a case of using a wireless-type receiver coil unit as well as a wired-type receiver coil unit can be treated as the transitionary phase in which a conventional MRI system representing the product and used in combination with a wired-type receiver coil unit gets substituted with a device in which a wireless-type receiver coil unit is used. Moreover, from the perspective of the cost of the entire system, using a wireless-type receiver coil unit as well as a wired-type receiver coil unit enables manufacturing the system at a lower cost.

Moreover, in the embodiment, it is assumed that the receiver coil unit 102 is battery-driven. However, the embodiment is not limited by that case. For example, even in the case in which the receiver coil unit 102 is driven by the electric power supplied from the main unit 101, the configuration of the receiver coil unit 102 according to the embodiment can still be implemented in an identical manner. In that case, it is believed that there is less demand for low power consumption as compared to the battery-driven configuration; and, as explained earlier, as a result of performing the phase control of the clock signals during only a specific period of time based on the pulse sequence information, at least it can be expected to hold down the heat generated in the receiver coil unit 102.

Meanwhile, in the explanation given above, a "processor" reads a computer program corresponding to the processing functions from a memory unit and executes the computer program. However, the embodiment is not limited by that case. Herein, the term "processor" implies, for example, a central processing unit (CPU), or a graphical processing unit (GPU), an ASIC, or a programmable logic device (such as an SPLD, a CPLD, or an FPGA). For example, when the processor is a CPU, it reads a computer program stored in the memory and executes it so as to implement the functions. On the other hand, when the processor is an ASIC, instead of reading a computer program from a memory unit, the processing functions are directly embedded as logic circuitries in the circuitry of the processor. Meanwhile, the processing units are not limited to be implemented using singular processors. Alternatively, for example, each processing unit can be configured by combining a plurality of independent processors each of which executes computer programs and implements corresponding functions. Moreover, a plurality of constituent elements illustrated in FIG. 1 can be integrated in a singular processor in which the respective processing functions can be implemented.

A computer program executed by a processor is stored in advance in a read only memory (ROM) or a memory unit. Alternatively, the computer program can be recorded as an installable file or an executable file in a computer-readable memory medium such as a compact disk-read only memory (CD-ROM), a flexible disk (FD), a compact disk recordable (CD-R), or a digital versatile disk (DVD). Still alternatively, the computer program can be stored in a downloadable manner in a computer connected to a network such as the Internet. The computer program is configured using, for example, modules of the function units explained earlier. As far as the actual hardware is concerned, a CPU reads the computer program from a memory medium such as a ROM and executes it, so that the modules are loaded and generated in a main memory device.

According to at least one of the aspects of the embodiment, while holding down the power consumption of the receiver coil unit, it becomes possible to reduce the clock phase shifting attributed to phasing and to enhance the accuracy of the reconstructed images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a main unit; and
a receiver coil unit that is a separate unit from the main unit, wherein
the main unit includes processing circuitry configure to
generate a first clock signal,
receive a clock signal sent by the receiver coil unit in a wireless manner, and generate a second clock signal,
perform, in a first time period which is based on pulse sequence information, phase control of a third clock signal, based on phase difference between the first clock signal and the second clock signal, and stop, in a second time period which is based on the pulse sequence information, the phase control,
send the third clock signal in a wireless manner to the receiver coil unit,
receive a magnetic resonance signal sent by the receiver coil unit in a wireless manner, and
process the magnetic resonance signal and reconstruct an image related to a subject.

2. A magnetic resonance imaging apparatus comprising:
a main unit; and
a receiver coil unit that is a separate unit from the main unit, wherein
the receiver coil unit includes processing circuitry configured to
receive a clock signal sent by the main unit in a wireless manner,
receive a magnetic resonance signal released in form of electromagnetic waves from a subject, and output a magnetic resonance signal in electric form,
digitize the magnetic resonance signal in synchronization with a clock signal sent by the main unit in a wireless manner,
send the digitized magnetic resonance signal in a wireless manner to the main unit,
in a first time period that is based on pulse sequence information, send a clock signal sent by the main unit in a wireless manner, to the main unit in a wireless manner, receive a third clock signal sent by the main unit in a wireless manner after phase control of the third clock signal is performed based on phase difference between a first clock signal generated by the main unit and a second clock signal generated based on the clock signal sent by the receiver coil, and digitize the magnetic resonance signal in synchronization with the third clock signal, and
in a second time period that is based on the pulse sequence, stop wireless transmission of a clock signal sent by the main unit in a wireless manner.

3. A magnetic resonance imaging apparatus comprising:
a main unit; and
a receiver coil unit that is a separate unit from the main unit, wherein
the main unit includes first processing circuitry configured to
generate a first clock signal,
receive a clock signal sent by the receiver coil unit in a wireless manner, and generate a second clock signal,
perform, in a first time period which is based on pulse sequence information, phase control of a third clock signal, based on phase difference between the first clock signal and the second clock signal, and stop, in a second time period which is based on the pulse sequence information, the phase control,
send the third clock signal in a wireless manner to the receiver coil unit,
receive a magnetic resonance signal sent by the receiver coil unit in a wireless manner, and
process the magnetic resonance signal and reconstruct an image related to a subject, and the receiver coil unit includes second processing circuitry configured to
receive a clock signal sent by the main unit in a wireless manner,
receive a magnetic resonance signal released in the form of electromagnetic waves from the subject, and output a magnetic resonance signal in electric form,
digitize the magnetic resonance signal in synchronization with a clock signal sent by the main unit in a wireless manner,
send the digitized magnetic resonance signal in a wireless manner to the main unit, and
send, in the first time period, a clock signal sent by the main unit in a wireless manner, to the main unit in a wireless manner, and stop, in the second time period, wireless transmission of a clock signal sent by the main unit in a wireless manner.

4. A control method for a magnetic resonance imaging apparatus including a main unit that includes processing circuitry, and a receiver coil unit that is a separate unit from the main unit, the method comprising:
generating a first clock signal, by the processing circuitry;
receiving a clock signal sent by the receiver coil unit in a wireless manner, and generating a second clock signal, by the processing circuitry;
performing, in a first time period which is based on pulse sequence information, phase control of a third clock signal, based on phase difference between the first clock signal and the second clock signal, and stopping, in a second time period which is based on the pulse sequence, the phase control, by the processing circuitry;
sending the third clock signal in a wireless manner to the receiver coil unit, by the processing circuitry;
receiving a magnetic resonance signal sent by the receiver coil unit in a wireless manner, by the processing circuitry; and
processing the magnetic resonance signal, and reconstructing an image related to a subject, by the processing circuitry.

5. A control method for a magnetic resonance imaging apparatus including a main unit, and a receiver coil unit that includes processing circuitry and is a separate unit from the main unit, the method comprising:
receiving a clock signal sent by the main unit in a wireless manner, by the processing circuitry;
receiving a magnetic resonance signal released in form of electromagnetic waves from a subject, and outputting a magnetic resonance signal in electric form, by the processing circuitry;
digitizing the magnetic resonance signal in synchronization with a clock signal sent by the main unit in a wireless manner, by the processing circuitry;
sending the digitized magnetic resonance signal in a wireless manner to the main unit, by the processing circuitry;
in a first time period that is based on pulse sequence information, sending a clock signal sent by the main unit in a wireless manner, to the main unit in a wireless manner, receiving a third clock signal sent by the main unit in a wireless manner after phase control of the third clock signal is performed based on phase difference between a first clock signal generated by the main unit and a second clock signal generated based on the clock signal sent by the receiver coil, and digitizing the magnetic resonance signal in synchronization with the third clock signal; and
in a second time period that is based on the pulse sequence, sending wireless transmission of a clock signal sent by the main unit in a wireless manner.

6. A control method for a magnetic resonance imaging apparatus including a main unit that includes first processing circuitry, and a receiver coil unit that includes second processing circuitry and is a separate unit from the main unit, the method comprising:
sending, in a first time period which is based on pulse sequence information, a clock signal sent by the main unit in a wireless manner, to the main unit in a wireless manner, and stopping, in a second time period which is based on the pulse sequence, wireless transmission of a clock signal sent by the main unit in a wireless manner, by the second processing circuitry;
generating a first clock signal, by the first processing circuitry;
receiving a clock signal sent by the receiver coil unit in a wireless manner, and generating a second clock signal, by the first processing circuitry;
performing, in a first time period which is based on pulse sequence information, phase control of a third clock signal, based on phase difference between the first clock signal and the second clock signal, and stopping, in a second time period which is based on the pulse sequence, the phase control, by the first processing circuitry;
sending the third clock signal in a wireless manner to the receiver coil unit, by the first processing circuitry;
receiving a clock signal sent by the main unit in a wireless manner, by the second processing circuitry;
receiving a magnetic resonance signal released in form of electromagnetic waves from a subject, and outputting a magnetic resonance signal in electric form, by the second processing circuitry;
digitizing the magnetic resonance signal in synchronization with a clock signal sent by the main unit in a wireless manner, by the second processing circuitry;
sending the digitized magnetic resonance signal in a wireless manner to the main unit, by the second processing circuitry;
receiving a magnetic resonance signal sent by the receiver coil unit in a wireless manner, by the first processing circuitry; and
processing the magnetic resonance signal, and reconstructing an image related to the subject, by the first processing circuitry.

7. The magnetic resonance imaging apparatus according to claim 3, wherein
the first processing circuitry is further configured to send, before start of imaging of a magnetic resonance image, the pulse sequence information in a wireless manner to the receiver coil unit, and
the second processing circuitry is further configured to receive the pulse sequence information sent by the main unit in a wireless manner.

8. The magnetic resonance imaging apparatus according to claim 1, wherein
the processing circuitry is further configured to set the first time period and the second time period, based on the pulse sequence information.

9. The magnetic resonance imaging apparatus according to claim 2, wherein
the processing circuitry is further configured to set the first time period and the second time period, based on the pulse sequence.

10. The magnetic resonance imaging apparatus according to claim 3, wherein
the first processing circuitry is further configured to set the first time period and the second time period, based on the pulse sequence information, and
the second processing circuitry is further configured to set the first time period and the second time period, based on the pulse sequence information.

11. The magnetic resonance imaging apparatus according to claim 10, wherein
the first processing circuitry and the second processing circuitry are configured to set the first time period, based on at least one of: a period of time for analog-to-digital conversion of a magnetic resonance signal as specified in the pulse sequence information; an operation response time of the first processing circuitry and the second processing circuitry; and a wireless signal propagation time of the first processing circuitry and the second processing circuitry.

12. The magnetic resonance imaging apparatus according to claim 10, wherein
the first processing circuitry is further configured to measure an operation response time and a wireless signal propagation time since start of the phase control until the phase control appears as phase variation of a second clock signal,
the first processing circuitry is further configured to send, before start of imaging of a magnetic resonance image, measurement result of the operation response time and the wireless signal propagation time in a wireless manner to the receiver coil unit,
the second processing circuitry is further configured to receive the measurement result sent by the main unit in a wireless manner, and
the first processing circuitry and the second processing circuitry are further configured to set the first time period, based on a period of time for analog-to-digital conversion of a magnetic resonance signal as specified in the pulse sequence information, and the measurement result.

* * * * *